United States Patent
Ein-Gal

(10) Patent No.: US 8,964,934 B2
(45) Date of Patent: Feb. 24, 2015

(54) CONE BEAM CT SCANNING

(71) Applicant: Moshe Ein-Gal, Ramat Hasharon (IL)

(72) Inventor: Moshe Ein-Gal, Ramat Hasharon (IL)

( * ) Notice: Subject to any disclaimer, the term of this patent is extended or adjusted under 35 U.S.C. 154(b) by 127 days.

(21) Appl. No.: 13/870,196

(22) Filed: Apr. 25, 2013

(65) Prior Publication Data

US 2014/0321605 A1  Oct. 30, 2014

(51) Int. Cl.
*G01V 5/00* (2006.01)
*G01N 23/04* (2006.01)

(52) U.S. Cl.
CPC .................................... *G01N 23/046* (2013.01)
USPC ................................................ 378/10; 378/4

(58) Field of Classification Search
CPC ..................................................... A61B 6/4028
USPC ........................................................ 378/4, 10
See application file for complete search history.

(56) References Cited

U.S. PATENT DOCUMENTS

| | | | |
|---|---|---|---|
| 7,170,966 B2 * | 1/2007 | Kuo-Petravic et al. | 378/4 |
| 7,688,939 B2 * | 3/2010 | Ein-Gal | 378/20 |
| 7,760,852 B2 * | 7/2010 | Chen et al. | 378/19 |

* cited by examiner

*Primary Examiner* — Hoon Song
(74) *Attorney, Agent, or Firm* — Dekel Patent Ltd.; David Klein

(57) ABSTRACT

A CBCT system is described that includes a radiation source for emitting a cone beam of radiation in a beam direction towards an object, a detector for detecting the cone beam of radiation, and a positioner for moving the radiation source and the object according to a scanning trajectory. The system is operated according to a sampling pattern that includes intersections of the scanning trajectory and a reconstruction trajectory, wherein motion of the radiation source is substantially confined to a spherical shell. The positioner moves the radiation source at a speed higher than a highest speed of the object by a factor of at least 10. The largest angular discrepancy between any vector in a range of the scanning trajectory and the nearest sample of the scanning trajectory does not exceed 10°, preferably 6° and more preferably 3°.

20 Claims, 3 Drawing Sheets

CONE BEAM CT SCANNING

FIELD OF THE INVENTION

The present invention generally relates to a method and system for cone beam computerized tomography (CBCT).

BACKGROUND OF THE INVENTION

Cone beam CT projections of an object are a function of scanning trajectory, that is, the relative positions of the irradiating source and the object. Generally, such a trajectory includes rotation about a rotational axis intersecting the object, similar to conventional CT. Of particular interest is imaging of a quasi-short object, which is the reconstruction of a short portion of a long object from longitudinally truncated cone beam data.

In a spherical coordinate system, the two angular coordinates of a trajectory sample, i.e., the angle in the fan direction (Phi—$\phi$) and the cone direction (Theta—$\theta$) can be viewed as a 2D vector in a Phi/Theta plane, and respective ranges of Phi and Theta define the trajectory range.

FIG. 1 illustrates examples of prior art scanning trajectories in terms of ($\phi$, $\theta$) coordinates. A simple CBCT trajectory is circular (indicated by reference numeral 1 in FIG. 1), consisting of a single revolution in the fan angle $\phi$ direction about a longitudinal axis of the object. Data sets (projections) associated with such a trajectory are theoretically insufficient for precise object reconstruction. However, approximate reconstructions such as the one suggested by L. A. Feldkamp, L. C. Davis, and J. W. Kress, "Practical cone-beam algorithm", JOSA A, Vol. 1, Issue 6, pp. 612-619 (1984), are commonly implemented. Such approximate algorithms may not be adequate for estimating object density values with sufficient precision required for radiotherapy treatment planning. Reconstruction error increases with increased beam cone angle.

Precise reconstruction algorithms require scanning trajectories incorporating sufficiently large Phi/Theta domain. Criteria for adequate CBCT scanning trajectories are described by Bruce D. Smith, "Image Reconstruction From Cone-Beam Projections: Necessary and Sufficient Conditions and Reconstruction Methods", IEEE Transactions on Medical Imaging, Volume MI-4, No. 1, pages 14-25 (March 1985). Helical trajectories (indicated by reference numeral 2 in FIG. 1), widely used in conventional CT scanning, are sufficient for precise CBCT reconstruction.

Saddle-curve cone-beam trajectory is described by Pack, J. D., F. Noo, and R Kudo, "Investigation of saddle trajectories for cardiac CT imaging in cone-beam geometry", Phys Med Biol, 2004, 49(11): pp. 2317-36, and by Yu, H. Y., et al., "Exact BPF and FBP algorithms for nonstandard saddle curves", Medical Physics, 2005, 32(11): pp. 3305-3312). Saddle curves can be directly implemented by rotating an x-ray source on a gantry about a rotational axis while simultaneously driving the source back and forth few times along the rotational axis.

Other trajectories typically related to motion of a single source have been described. For example, U.S. Pat. No. 7,782,999 to Lewalter et al. describes a hybrid system incorporating mechanical source housing rotation about the object and electronic beam steering along the rotational axis. U.S. Pat. No. 5,278,884 to Eberhard et al. describes sinusoidal, square wave (indicated by reference numeral 3 in FIG. 1), circular, and arc trajectories on a sphere. U.S. Pat. No. 7,197,105 to Katsevich describes a scanning trajectory composed of a curve on a plane (e.g., a plane orthogonal to a rotational axis) and of a line perpendicular to the plane. U.S. Pat. No. 6,983,034 to Wang et al. describes substantially circular, helical, spiral, or spiral-like scanning trajectories. U.S. Pat. No. 6,580,777 to Ueki et al. describes rotating the source about an object while simultaneously tilting the rotational axis relative to the object. US Patent Application 2010/0202583 to Wang et al. describes combined rotation of a source about the object and in a plane facing the object.

Trajectory samples form a sampling pattern on the Phi/Theta plane. The pattern density can be defined as the maximal distance between any vector in the trajectory domain and the nearest trajectory sample.

Typical CBCT scanning trajectories (such as the one ones mentioned above) are low density: the associated density is much larger than the space between subsequent samples. Consequently, the associated sampling patterns are uniquely related to the respective trajectories such that reconstruction algorithms designed for a particular trajectory cannot be used for another—the respective sampling patterns are too different.

An example of prior art low-density pattern is seen in FIG. 2, which illustrates a sampling pattern of a low-density triangular wave trajectory.

Characterizing data acquisition geometry only by scanning trajectory assumes adequate detector size and positioning. U.S. Pat. No. 6,041,097 to Roos et al. describes using a flat panel detector for CBCT. Cone beam magnification requires large area detectors for CBCT. Detector width reduction may be achieved by incorporating multiple sources irradiating the object from different angles. For example, U.S. Pat. No. 7,106,825 to Gregerson et al. describes a combination of several smaller detectors. U.S. Pat. No. 7,760,852 to Chen et al. describes a half-width detector combined with a full circular trajectory. U.S. Pat. No. 7,639,775 to DeMan et al. describes offset sources respectively operable to irradiate object radial segments. U.S. Pat. No. 7,062,006 to Pelc et al. describes inverse geometry CT incorporating 2D array of radiation sources configured to respectively emit finely-collimated beams toward a common small detector.

SUMMARY OF THE INVENTION

The present invention seeks to provide improved methods and devices for cone beam CT (CBCT), as is described more in detail hereinbelow.

In accordance with one non-limiting embodiment of the invention, scanning trajectories include object rotation about a rotational axis at one speed and periodic rotation of a radiation source at a much higher speed.

High-density sampling patterns, obtained by intersecting a scanning trajectory of the invention with any other scanning trajectory, enables using reconstruction algorithms designed for the other scanning trajectory. This is in contradistinction to the prior art, wherein, as mentioned in the background, reconstruction algorithms designed for one scanning trajectory cannot be used for another scanning trajectory.

There is provided in accordance with a non-limiting embodiment of the invention, a cone beam computerized tomography (CBCT) system including a radiation source for emitting a cone beam of radiation in a beam direction towards an object, a detector for detecting the cone beam of radiation, a positioner for moving the radiation source and the object according to a scanning trajectory, and a controller in communication with the positioner, the controller operable to operate the radiation source according to a sampling pattern that includes intersections of the scanning trajectory and a reconstruction trajectory, wherein motion of the radiation source is substantially confined to a spherical shell, wherein a center of the sphere substantially coincides with a center of the detector, and wherein the beam direction substantially intersects the detector center, and wherein the positioner is operable to move the radiation source at speed higher than a highest speed of the object by a factor of at least 10, and wherein a largest angular discrepancy between any vector in a range of the scanning trajectory and a nearest sample of the scanning trajectory does not exceed 10°, preferably 6° and more preferably 3°.

There is also provided in accordance with a non-limiting embodiment of the invention, a method for CBCT including emitting a cone beam of radiation from a radiation source in a beam direction towards an object, detecting the cone beam of radiation with a detector, moving the radiation source and the object according to a scanning trajectory, and operating the radiation source according to a sampling pattern that includes intersections of the scanning trajectory and a reconstruction trajectory, wherein motion of the radiation source is substantially confined to a spherical shell, wherein a center of the sphere substantially coincides with a center of the detector, and wherein the beam direction substantially intersects the detector center, and wherein the radiation source is moved at speed higher than a highest speed of the object by a factor of at least 10, and wherein a largest angular discrepancy between any vector in a range of the scanning trajectory and a nearest sample of the scanning trajectory does not exceed 10°, preferably 6° and more preferably 3°.

BRIEF DESCRIPTION OF THE DRAWINGS

The present invention will be understood and appreciated more fully from the following detailed description, taken in conjunction with the drawing in which.

DETAILED DESCRIPTION OF EMBODIMENTS

Figure 1:
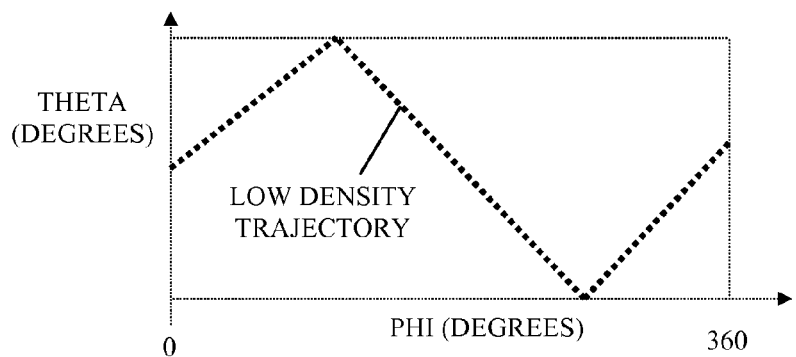
FIG. 1 is a simplified graphical illustration of examples of prior art scanning trajectories in terms of ($\phi$, $\theta$) coordinates.
Figure 2:
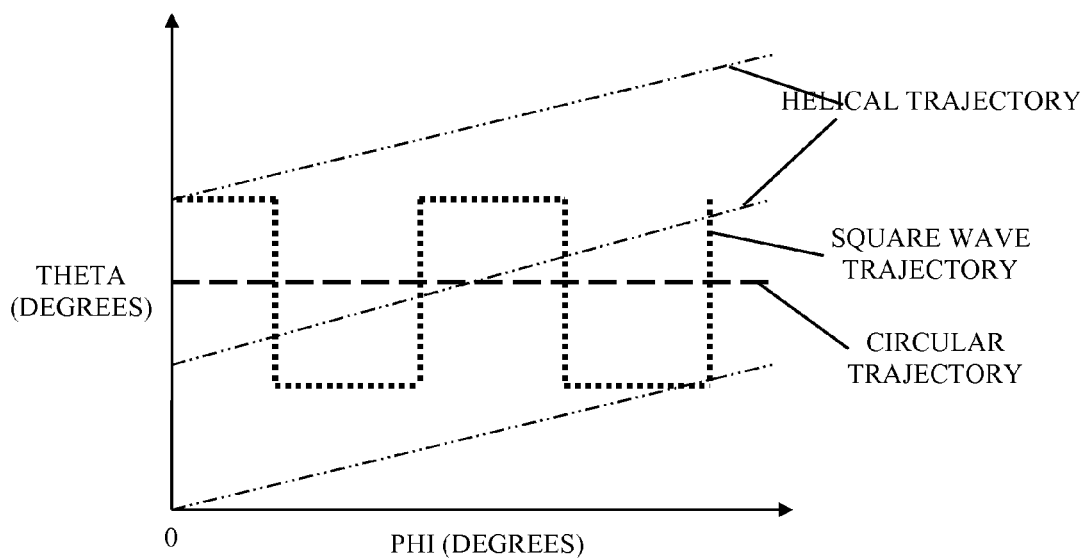
FIG. 2 is a simplified graphical illustration of a sampling pattern of a low-density triangular wave trajectory of the prior art.
Figure 3:
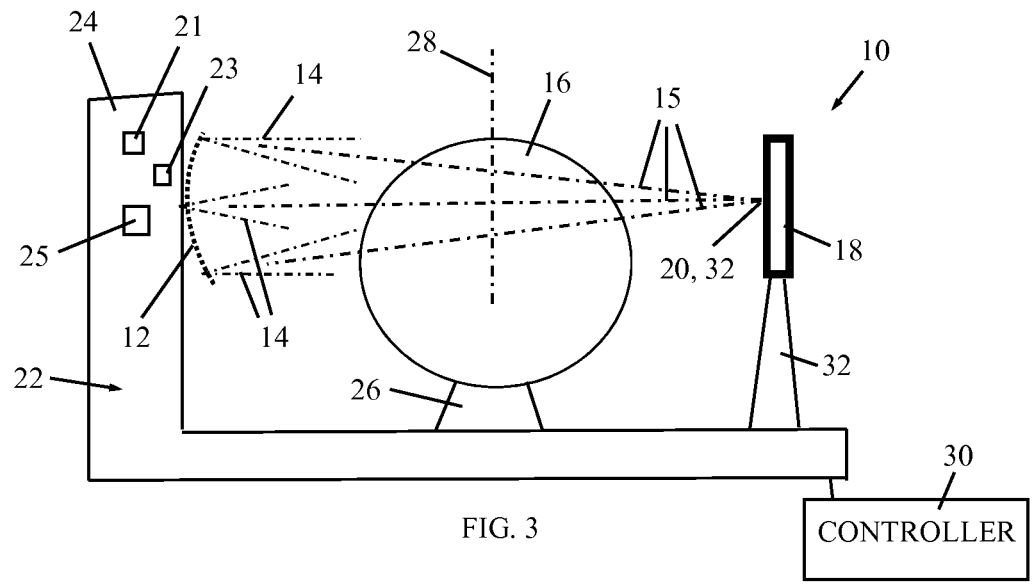
FIG. 3 is a simplified pictorial illustration of a cone beam CT (CBCT) scanner system, which uses a small detector, constructed and operative in accordance with an embodiment of the present invention.

Reference is now made to FIG. 3, which illustrates a cone beam CT (CBCT) scanner system 10, constructed and operative in accordance with an embodiment of the present invention.

CBCT system 10 includes a radiation source 12 (such as, but not limited to, an X-ray source) that emits a cone beam 14 of radiation in a beam direction 15 towards an object 16, such as an animate object (e.g., human or animal) or an inanimate object. A detector 18 is provided on the other side of object 16 and has a detector center 20. Detector 18 detects the cone beam(s) 14 of radiation, which pass through, off, over or around object 16.

CBCT system 10 includes a positioner 22 that can move radiation source 12 and the object 16 according to a scanning trajectory. Without limitation, positioner 22 includes a gantry 24, which moves the housing which houses the radiation source 12. Motion of the source housing may be implemented by electronically moving the source position. To achieve that, gantry 24 may include electron optics 21 operable to focus and deflect an electron beam in vacuum toward a radiation-producing target 23 or toward a set of discrete radiation-producing targets 23 so as to produce and emit cone beams 14 from desired locations. Gantry 24 may also include a sequencer 25 that sequentially triggers multiple radiation sources 12.

Without limitation, positioner 22 includes a turntable 26 that can rotate the object 16 about a rotational axis 28, such as a vertical rotational axis or any other suitable axis.

A controller (processor) 30 is in communication with positioner 22. Controller 30 can control operation of radiation source 12 according to a sampling pattern, which incorporates intersections of the scanning trajectory and a reconstruction trajectory. In another embodiment, controller 30 (or another processor) is in communication with detector 18. In such an embodiment, controller 30 receives detector data related to the sampling pattern and reconstructs the object or a portion thereof according to reconstruction algorithms related to the reconstruction trajectory.

In one embodiment of the scanning trajectory, the motion of radiation source 12 is substantially confined to a spherical shell that has a sphere center 32. In a preferred embodiment, the sphere center 32 coincides with the detector center 20, but the invention also encompasses a trajectory in which the sphere center 32 does not coincide with the detector center 20. As seen in FIG. 3, the beam directions 15 substantially intersect the detector center 20.

Positioner 22 moves radiation source 12 at speed higher than the highest speed of the movement of object 16 by a factor of at least 10. The largest angular discrepancy between any vector in the range of the scanning trajectory and the nearest sample of the scanning trajectory does not exceed 10°, preferably 6° and more preferably 3°.

In one embodiment, detector 18 is detached from the moving source 12 and the detector center 20 is stationary. In another embodiment, positioner 22 can move not only the radiation source 12, but also the object 16 and the detector 18. For example, positioner 22 can include a detector positioner 32 (e.g., another turntable) for rotating detector 18. Detector positioner 32 can position detector 18 so as to face radiation source 12. In one embodiment, positioner 22 can rotate radiation source 12 and detector 18 about a vertical rotational axis.

In the embodiment illustrated in FIG. 3, the CBCT scanner system 10 uses a small detector 18. Orthogonal motion components of the radiation source 12 relative to the rotational axis 28 allow reduction of detector width.

Figure 4:
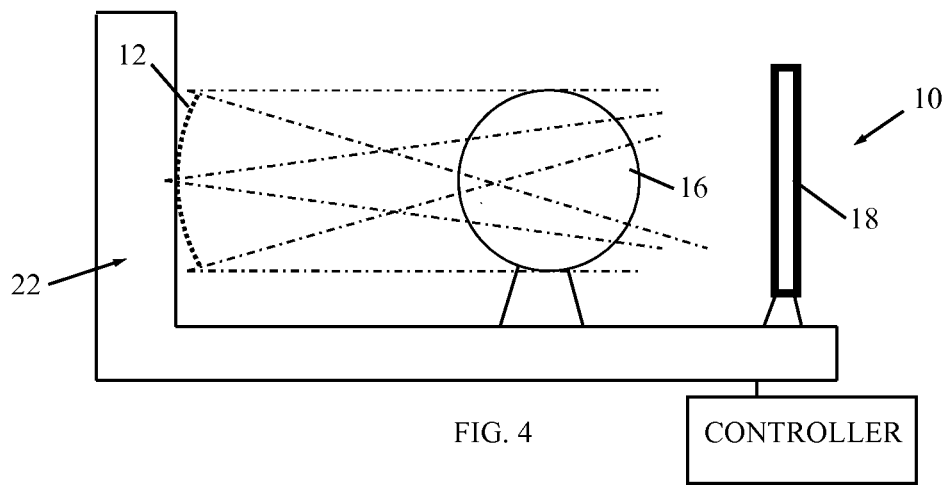
FIG. 4 is a simplified pictorial illustration of a CBCT scanner system, which uses a large detector, constructed and operative in accordance with an embodiment of the present invention.

In the embodiment of FIG. 4, CBCT scanner system 10 uses a large detector 18. In any of the embodiments of the invention, the positioner 22 can move the radiation source 12 in a reciprocating motion. For example, the reciprocating motion may be along an azimuthal, circular arc that has a circle center which coincides with the detector center.

Figure 5:
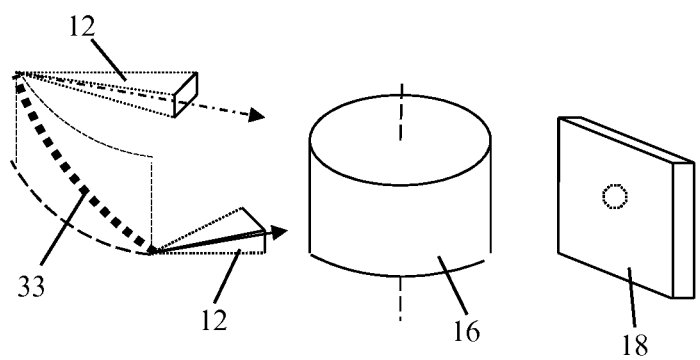
FIG. 5 is a simplified pictorial illustration of a CBCT scanner system, which uses a source oscillating on a tilted arc, constructed and operative in accordance with an embodiment of the present invention.

Reference is now made to FIG. 5, which illustrates a CBCT scanner system, which uses the radiation source 12 oscillating on a tilted arc 33 (that is, tilted away from the horizontal or vertical plane).

Figure 6:
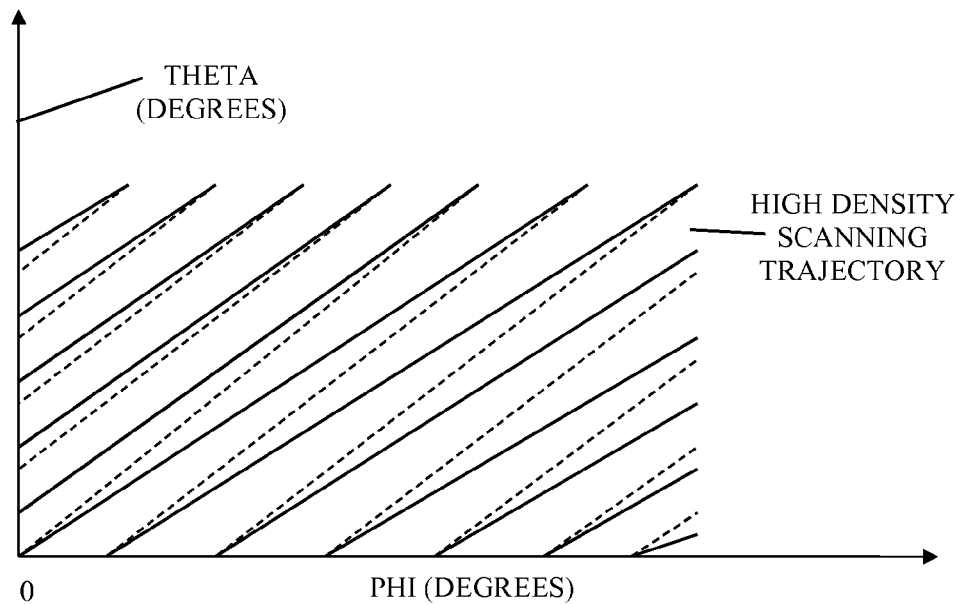
FIG. 6 is a simplified graphical illustration of a high density scanning trajectory in the Phi/Theta plane, in accordance with an embodiment of the present invention.

Reference is now made to FIG. 6, which illustrates a high density scanning trajectory in the Phi/Theta plane, in accordance with an embodiment of the present invention. The trajectory extends to a maximum cone angle through an entire 360° range of fan angles.

Figure 7:
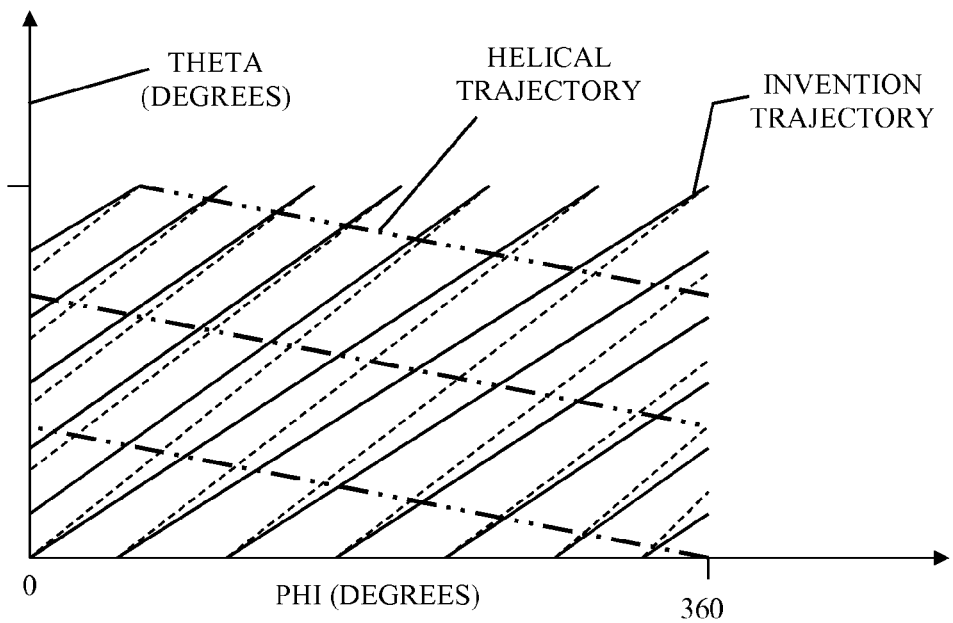
FIG. 7 is a simplified graphical illustration of a scanning trajectory of the invention intersecting with a helical reconstruction trajectory, in accordance with an embodiment of the present invention.

Reference is now made to FIG. 7, which illustrates a scanning trajectory of the invention (e.g., that of FIG. 6) intersecting with a helical reconstruction trajectory, in accordance with an embodiment of the present invention. Here again, the trajectory extends to a maximum cone angle through an entire 360° range of fan angles. High-density sampling patterns, obtained by intersecting the scanning trajectory of the invention with any other scanning trajectory, enables using reconstruction algorithms designed for the other scanning trajectory.

What is claimed is:

1. A cone beam computerized tomography (CBCT) system comprising:
    a radiation source for emitting a cone beam of radiation in a beam direction towards an object;
    a detector for detecting said cone beam of radiation;
    a positioner for moving said radiation source and said object according to a scanning trajectory; and
    a controller in communication with said positioner, said controller operable to operate said radiation source according to a sampling pattern that includes intersections of the scanning trajectory and a reconstruction trajectory,
    wherein motion of said radiation source is substantially confined to a spherical shell, and wherein said positioner is operable to move said radiation source at speed higher than a highest speed of the object by a factor of at least 10, and wherein a largest angular discrepancy between any vector in a range of the scanning trajectory and a nearest sample of the scanning trajectory does not exceed 10°.

2. The system according to claim 1, wherein the largest angular discrepancy between any vector in the range of the scanning trajectory and the nearest sample of the scanning trajectory does not exceed 6°.

3. The system according to claim 1, wherein the largest angular discrepancy between any vector in the range of the scanning trajectory and the nearest sample of the scanning trajectory does not exceed 3°.

4. The system according to claim 1, wherein said positioner is operable to rotate the object about a vertical rotational axis.

5. The system according to claim 1, wherein said detector center is stationary.

6. The system according to claim 1, wherein said positioner is operable to rotate said radiation source and said detector about a vertical rotational axis.

7. The system according to claim 1, wherein said positioner is operable to cause reciprocating motion of said radiation source along an arc.

8. The system according to claim 7, wherein said arc is tilted away from a horizontal or vertical plane.

9. The system according to claim 7, wherein said arc is circular with a circle center, and the circle center coincides with a center of the detector.

10. The system according to claim 1, further comprising a detector positioner operable to position said detector so as to face said radiation source.

11. The system according to claim 1, wherein said positioner comprises at least one of a device for moving a radiation source housing, electron optics operable to focus and deflect an electron beam in vacuum toward a radiation-producing target or toward a set of discrete radiation-producing targets, and a sequencer operable to sequentially trigger multiple radiation sources.

12. The system according to claim 1, further comprising a processor in communication with said detector, the processor operable to receive detector data related to the sampling pattern and reconstruct the object or a portion thereof according to reconstruction algorithms related to the reconstruction trajectory.

13. A method for CBCT comprising:
    emitting a cone beam of radiation from a radiation source in a beam direction towards an object;
    detecting said cone beam of radiation with a detector;
    moving said radiation source and said object according to a scanning trajectory; and
    operating said radiation source according to a sampling pattern that includes intersections of the scanning trajectory and a reconstruction trajectory,
    wherein motion of said radiation source is substantially confined to a spherical shell, and wherein said radiation source is moved at speed higher than a highest speed of the object by a factor of at least 10, and wherein a largest angular discrepancy between any vector in a range of the scanning trajectory and a nearest sample of the scanning trajectory does not exceed 10°.

14. The method according to claim 13, wherein the largest angular discrepancy between any vector in the range of the scanning trajectory and the nearest sample of the scanning trajectory does not exceed 6°.

15. The method according to claim 13, wherein the largest angular discrepancy between any vector in the range of the scanning trajectory and the nearest sample of the scanning trajectory does not exceed 3°.

16. The method according to claim 13, wherein said object is rotated about a vertical rotational axis.

17. The method according to claim 13, wherein said detector center is stationary.

18. The method according to claim 13, wherein said radiation source is moved in a reciprocating motion along an arc.

19. The method according to claim 18, wherein said arc is tilted away from a horizontal or vertical plane.

20. The method according to claim 1, further comprising receiving detector data related to the sampling pattern and reconstructing the object or a portion thereof according to reconstruction algorithms related to the reconstruction trajectory.

* * * * *